United States Patent [19]

Huber

[11] 4,350,718

[45] Sep. 21, 1982

[54] METHOD OF FABRICATING GRAPHITE TUBE

[75] Inventor: Bernhard Huber, Überlingen, Fed. Rep. of Germany

[73] Assignee: Bodenseewerk Perkin-Elmer & Co. GmbH, Fed. Rep. of Germany

[21] Appl. No.: 304,518

[22] Filed: Sep. 21, 1981

Related U.S. Application Data

[63] Continuation of Ser. No. 245,790, Mar. 20, 1981, abandoned.

[30] Foreign Application Priority Data

Mar. 20, 1980 [DE] Fed. Rep. of Germany ....... 3010717

[51] Int. Cl.$^3$ .......................... B05D 7/22; B05D 3/02
[52] U.S. Cl. .................................. 427/181; 427/226; 427/228; 427/237; 427/249
[58] Field of Search ............... 427/181, 237, 226, 228, 427/249

[56] References Cited

U.S. PATENT DOCUMENTS 3,860,437   1/1975   Gust ................................ 427/237 X

*Primary Examiner*—James R. Hoffman
*Attorney, Agent, or Firm*—S. A. Giarratana; F. L. Masselle; R. A. Hays

[57] ABSTRACT

A method for coating a graphite tube for use in atomic absorption spectroscopy includes forming a layer of an adhesive volatile material on the tube. An inert material, in the form of a powder, is applied to the layer and heated to pyrolyze the inert material. Thereafter, the graphite tube is coated with pyrolytic graphite.

10 Claims, No Drawings

METHOD OF FABRICATING GRAPHITE TUBE

This application is a continuation of Application Ser. No. 245,790, filed Mar. 20, 1981, now abandoned.

The present invention generally relates to a method for producing coated graphite tubes for use in flameless atomic absorption spectroscopy and, in particular, relates to a method in which a graphite tube is first coated with an inert material and thereafter heated while an inert gas flow containing a carbonaceous gas is passed therethrough.

It is presently known that the useful life of graphite tubes for use in atomic absorption spectroscopy can be increased by coating the inner wall thereof with pyrolytic graphite.

To this end, a flow of inert gas, such as argon, which comprises an admixture of 5 or 10 percent of volume of a carbonaceous gas, such as methane, is passed through a graphite tube, which is heated to temperatures up to 2150° C. with respect to a step program (Angewandte Atom Absorptions-Spektroskopie, Bodenseewerk Perkin-Elmer & Co. GmbH, 1979, No. 12). This treatment can be preformed in the graphite tube atomizer of an atomic absorption spectrometer.

A further improvement of the useful life of graphite tubes is achieved by applying to a base plate a high-melting inert metal carbide (German Offenlegungsschrift 29 11 460). To this end the graphite is often initially coated with an appropriate metal such as titanium, zirconium, hafnium, vanadium, niobium, tantalum, tungsten or molybdenum. In the prior art, the coating is fabricated by vacuum evaporation or by direct current evaporation. The method of such a fabrication usually requires rather complicated equipment operated under high vacuum. After the coating process, the graphite tubes are then inserted into an induction furnace and, while argon is passed therethrough, are heated to a high temperature whereat carbide is formed. Subsequently, or simultaneously, pyrolytic graphite is deposited on the carbide base plate, while methane is admixed to the argon flow.

SUMMARY OF THE INVENTION

In view of the above, it is one object of the present invention to provide a simplified method by which graphite tubes having a pyrolytic graphite are obtained on an inert base plate with simple and easily available means.

Accordingly, this object is accomplished at least in part, by first providing the graphite tube with an adhesive layer of material which is volatile on heating and which possibly leaves only a carbon residue. The inert material is applied to the adhesive layer in powder form and the graphite tube, with the adhesive layer and the inert material adherent thereto, is heated to between 1500° C. and 2500° C. Thereafter, it is coated with pyrolytic graphite.

According to the invention, the graphite tube is directly converted with the powder material, which also can be a carbide forming metal, such that it is not required to coat the graphite tube on its surface with the inert material in a special apparatus under high vacuum. Because the usable materials can usually be obtained in powder form, this results in a substantial time saving and an economy of expenses, because no expensive, rather complicated vacuum evaporation equipment is required therefor. With appropriate method execution all steps required for heat treatment of the graphite tube can take place using the heat device already available in the atomic absorption spectrometer.

Other objects and advantages will become apparent from the following detailed description.

DETAILED DESCRIPTION OF THE INVENTION

The following embodiment describes a method which can be executed in a normally equipped laboratory with simple means and auxiliary materials;

EXAMPLE

Ten grams of commercial beeswax are initially dissolved in about 100 ml of benzine by stirring. A conventional graphite tube is then immersed in the solvent and removed after some minutes and dried in the air. The dried graphite tube, which is now coated with a beeswax layer, is placed in a beaker containing commercial, fine-granular tungsten powder (preferably having an average grain diameter of about 0.5 mm). Preferably, the beaker is shaken to ensure distributing of the tungsten powder over the faces covered by the beeswax and adhering thereon. After some minutes, the tungsten powder is removed. The graphite tube with the wax layer now covered with tungsten powder is next inserted into a graphite tube atomizer, such as, for example, an HGA-72 of a Perkin-Elmer atomic absorption spectrometer. Thereafter, while an argon flow is passed through (1 liter per min) the tube is heated in steps corresponding to the method used in the measurement of the atomic absorption, to a final temperature of 1900° C. By this method, the beeswax is pyrolyzed and the gaseous pyrolyzed products escape without loosening the tungsten powder and are removed with the argon flow, so that only carbon remains as a pyrolyzed residue. The remaining carbon forms a compound with the graphite tube and the tungsten powder. The compound is a layer of tungsten carbide strongly tied in the surface of the graphite tube at a defined temperature. After the temperature of 1900° C. has been reached, a flow of an argon methane mixture (0.25 ml/min 90 percent of volume argon, 10 percent of volume methane) is then passed through the graphite tube, pyrolytic graphite thus being deposited on the tungsten carbide layer.

In another embodiment of the example, the tungsten powder is initially mixed with an appropriate base to form a varnish, which is then coated onto the graphite tube. The coated graphite is then treated in the manner corresponding to the previous embodiment. The coating can be applied to an especially simple manner in that the graphite tube, after being inserted into the graphite tube atomizer, is heated with constant heating flow, which is set for the final temperature of 1900° C., while an argon flow is passed therethrough for about 10 seconds.

Alternatively, the graphite tube can be coated in a corresponding manner with inert material such as boron nitride, boron carbide or an appropriate ceramic material, without the inert layer having to be formed by a chemical reaction on the inner surface of the graphite tube.

In a further variation of the method, the graphite tube is introduced into a packing of powdery metal, for example tungsten powder, and is heated in this packing to a temperature sufficient for the carbide formation by an inert gas as argon in a furnace. The temperature and the duration of heating are selected corresponding to the respective desired layer thickness of the carbide. Normally, temperatures in the range between 1500° C. and 2500° C. are sufficient.

After cooling down, the graphite tube is removed from the packing and is then heated in known manner in a methane-comprising inert gas flow to temperatures in the range of about 2000° C., a sufficient layer of pyrolytic graphite being deposited on the carbide base plate after about 15 to 30 min.

The above described examples are intended to be illustrative examples only. It will become obvious to those skilled in the art that many other variations may be practical and useful. The scope of this invention is thus to be limited only by the appended claims and the reasonable interpretation thereof.

What is claimed is:

1. Method of coating a graphite tube, said method comprising the steps of:
    forming a layer of adhesive, volatile material on said graphite tube;
    applying a powder of inert material to said layer;
    pyrolyzing, in the presence of an inert gas flow, said layer; and thereafter
    coating said graphite tube with pyrolytic graphite.

2. Method as claimed in claim 1 wherein said adhesive, volatile layer includes beeswax.

3. Method as claimed in claim 2 wherein said applying step includes immersing said graphite tube in a solution of beeswax.

4. Method as claimed in claims 1, 2 or 3 further including the step of admixing a carbonaceous gas with said inert gas during said coating step.

5. Method as claimed in claim 4 wherein said graphite tube is heated to about 1900° C., said inert gas is argon and said carbonaceous gas is methane in an admixture of up to 10 percent by volume.

6. Method as claimed in claim 1 wherein said graphite tube is heated in a graphite tube atomizer of an atomic absorption spectrometer.

7. Method as claimed in claim 1 wherein said inert material is a high-melting carbide.

8. Method as claimed in claim 1 wherein said inert material is a ceramic material.

9. Method as claimed in claim 1 wherein said inert material is tungsten.

10. Method as claimed in claim 9 wherein said applying step includes introducing said graphite tube into a packing of carbide forming metal in powder form and heating said tube therein to the temperature whereat a superficial carbide is formed.

* * * * *